(12) United States Patent
Grunhut et al.

(10) Patent No.: US 11,426,531 B2
(45) Date of Patent: Aug. 30, 2022

(54) MEDICAL INJECTOR CAP REMOVER

(71) Applicant: Becton Dickinson France, Le Pont de Claix (FR)

(72) Inventors: Guillaume Grunhut, Grenoble (FR); Lionel Maritan, Pierre-Chatel (FR); Julien Singer, Domene (FR)

(73) Assignee: Becton Dickinson France, Le Pont de Claix (FR)

( * ) Notice: Subject to any disclaimer, the term of this patent is extended or adjusted under 35 U.S.C. 154(b) by 0 days.

(21) Appl. No.: 17/097,867

(22) Filed: Nov. 13, 2020

(65) Prior Publication Data

US 2021/0060262 A1 Mar. 4, 2021

Related U.S. Application Data

(63) Continuation of application No. 15/995,500, filed on Jun. 1, 2018, now Pat. No. 10,864,329.

(30) Foreign Application Priority Data

Jun. 2, 2017 (EP) ..................................... 17305656

(51) Int. Cl.
*A61M 5/32* (2006.01)
*A61M 5/31* (2006.01)

(52) U.S. Cl.
CPC ........ *A61M 5/3204* (2013.01); *A61M 5/3129* (2013.01); *A61M 5/3213* (2013.01);
(Continued)

(58) Field of Classification Search
CPC .............. A61M 5/3204; A61M 5/3213; A61M 5/3129; A61M 2005/3215; A61M 5/3205;
(Continued)

(56) References Cited

U.S. PATENT DOCUMENTS 5,305,766 A * 4/1994 Hahn .................. A61M 5/3213
128/919
2018/0133407 A1* 5/2018 Kemp ................. A61M 5/2033
(Continued)

FOREIGN PATENT DOCUMENTS

CN 209060215 U 7/2019
EP 2671606 A1 12/2013
(Continued)

OTHER PUBLICATIONS

Merceille, "Stelmi Rigid Needle Shield: The Successful Concept With The Anti Pop-Off Patented Design", 2008, "Prefilled Syringes: The Container of Choice for Today's Injectables", 14-16 (Year: 2008).*
(Continued)

*Primary Examiner* — Theodore J Stigell
*Assistant Examiner* — Rachel T. Smith
(74) *Attorney, Agent, or Firm* — The Webb Law Firm

(57) ABSTRACT

A cap remover for removing a cap covering a needle of a medical injector includes a body having an insertion portion at its proximal end configured to at least partially accommodate the cap, and a grabbing portion at its distal end having an internal cavity which includes an extraction member having a series of laminas extending radially and inwardly from a ring.

20 Claims, 5 Drawing Sheets

(52) U.S. Cl.
CPC ... *A61M 5/3205* (2013.01); *A61M 2005/3215* (2013.01); *A61M 2205/586* (2013.01)

(58) Field of Classification Search
CPC ............ A61M 2205/586; A61M 5/178; A61M 5/3202; A61M 5/321
See application file for complete search history.

(56) References Cited

U.S. PATENT DOCUMENTS

| | | |
|---|---|---|
| 2018/0344947 A1 | 12/2018 | Grunhut et al. |
| 2018/0353705 A1 | 12/2018 | Andre et al. |

FOREIGN PATENT DOCUMENTS

| | | | | |
|---|---|---|---|---|
| WO | WO-03051423 A2 | * | 6/2003 | .......... A61M 5/3202 |
| WO | 2016193353 A1 | | 12/2016 | |

OTHER PUBLICATIONS

Polymers—Physical Properties, https://www.engineeringtoolbox.com/polymer-properties-d_1222.html (Year: 2020).*

BHN—Brinell Hardness Number, https://www.engineeringtoolbox.com/bhn-brinell-hardness-number-d_1365.html (Year: 2020).*

Young's Modulus of Steel, https://www.amesweb.info/Materials/Youngs-Modulus-of-Steel.aspx (Year: 2020).*

"Hook", https://www.merriam-webster.com/dictionary/hook (Year: 2021).*

Merceille, "Stelmi Rigid Needle Shield: The Successful Concept With The Anti Pop-Off Patented Design", 2008, "Prefilled Syringes: The Container of Choice for Today's Injectables", pp. 14-16 (Year 2008).

Young's Modulus of Steel, https://www.amesweb.info/Materials/Youngs-Modulus-of-steel.aspx (Years 2020).

* cited by examiner

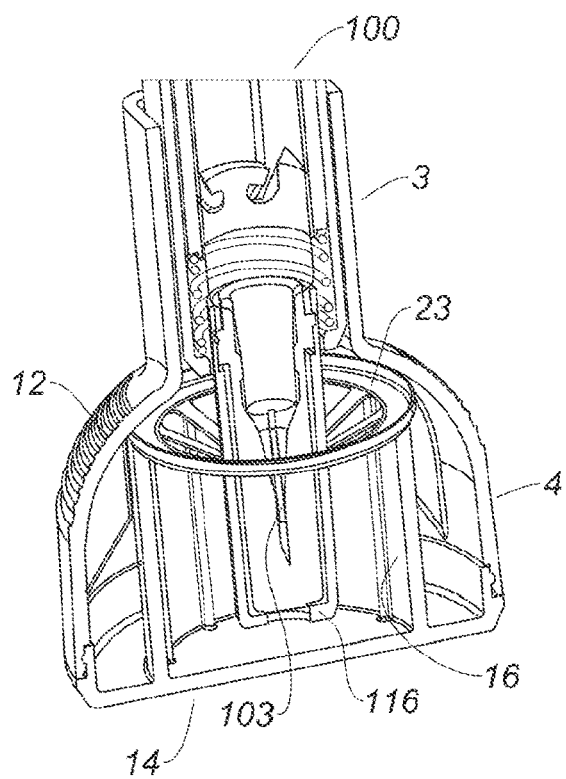
Fig. 4
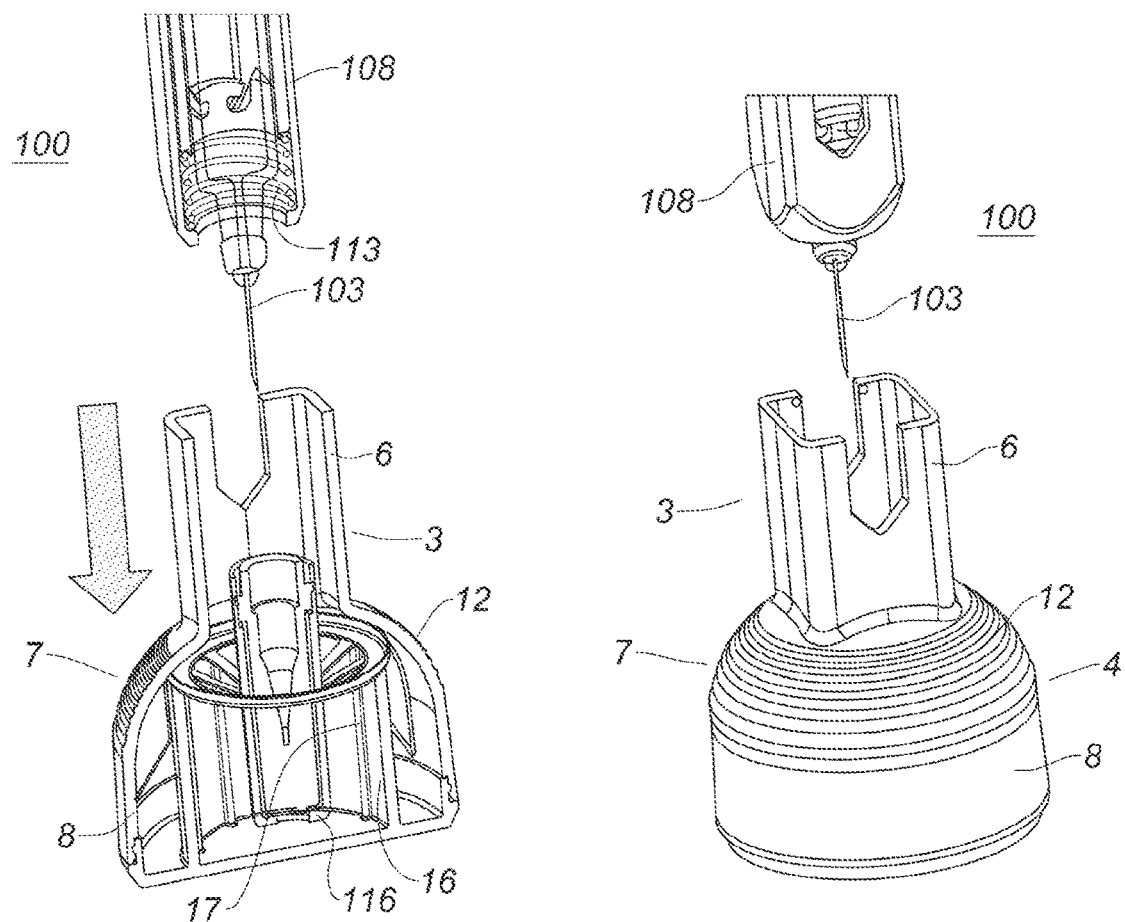
Fig. 5
Fig. 6

MEDICAL INJECTOR CAP REMOVER

CROSS-REFERENCE TO RELATED APPLICATION

This application is a continuation of U.S. patent application Ser. No. 15/995,500 filed Jun. 1, 2018, which claims priority to European Patent Application No. 17305656.5 filed Jun. 2, 2017, the disclosure of which is hereby incorporated in its entirety by reference.

BACKGROUND OF THE INVENTION

Field of the Invention

The present disclosure relates generally to a cap remover for a medical injector.

Description of Related Art

Medical injectors are widely used to deliver doses of fluids such as liquid medicaments or vaccinations to a patient.

Medical injectors typically comprise a standard plastic or glass prefilled barrel tipped with an injection needle.

Medical injectors may be configured as syringes, syringes provided with a safety device, auto-injectors or pen injectors intended for self-administration by patients or by untrained personnel.

In order to maintain sterility prior to use and to reduce the risk of incurring an accidental needle-stick, protection of the needle tip is important. Medical injectors are typically supplied with a rubber or plastic cap which guards the needle prior to use.

Immediately prior to use, a user must remove the protective cap from the injector.

The operation whereby the user—patient, untrained personnel or medical staff—removes the protective cap requires some operational skill from the user, as the protective cap is usually a piece of small dimensions and because the protective cap is engaged and is maintained via a friction fit with the injector's tip.

The manipulation of a standard prior art injector device can thus be inconvenient, particularly where the injection is self-administered by the patient or by untrained personnel. Users with impaired finger skills may find difficulty in removing a protective cap from an injector device or syringe.

SUMMARY OF THE INVENTION

In this context, an object of the present disclosure includes improving the operation of removing a cap from a medical injector.

A first aspect of the disclosure concerns a cap remover for removing a protective cap covering a needle of a medical injector, the cap remover including:

an outer body including:
a proximal end and a distal end;
an insertion portion defining a cavity configured to guide the protective cap from the proximal end of the outer body toward a central opening sized and shaped to receive the protective cap;
a grabbing portion including at least an outer grabbing surface configured to be grabbed by a user; and
an extraction member positioned within the outer body at a distal end of the insertion portion, the extraction member including:
an annular ring fixed to the outer body; and
a plurality of flexible metallic laminas extending radially and inwardly from the annular ring toward the central opening, the laminas defining a frustoconical envelope between the annular ring and the central opening.

Advantageously, the metallic laminas are configured:
to flex outwardly and slide on the protective cap when the protective cap is inserted into the cap remover; and
to stick into the protective cap when the protective cap is removed from the needle.

Advantageously, each lamina presents a stiffness of between 2 N and 30 N in order to be able to flex and slide onto the protective cap during insertion of the protective cap into the central opening.

Advantageously, each lamina presents a Young's modulus of between 190 GPa and 230 GPa in order to be able to stick themselves into the protective cap during removal of the protective cap.

Advantageously, the annular ring defines a transversal plane, each lamina forming an angle α of between 15° and 60° with the transversal plane, and preferably of 28°. This angle is preferred in order to facilitate insertion of the protective cap into the cap remover while allowing gripping of the protective cap by the laminas during removal of the protective cap.

Advantageously, the extraction member includes between eight and twelve laminas, and preferably includes ten laminas in order to center and axially guide the protective cap into the central opening.

Advantageously, each lamina includes a sharp tip in order to be able to stick into the protective cap.

Advantageously, the extraction member is made of stainless steel, in order to have laminas that are flexible but can embed themselves into a plastic protective cap.

Advantageously, the laminas are configured to exert on the protective cap a clamping force of between 20 N and 300 N, so as to be able to pull the protective cap from the medical injector.

Advantageously, the laminas are sized so that, before insertion of the protective cap, the central opening presents a diameter of between 78% and 95% of the diameter of the protective cap. This ratio enables insertion of the protective cap into the central opening, but also it enables the laminas to clamp the protective cap in order to remove it.

Advantageously, the central opening is located distally from the annular ring.

According to different embodiments:
the outer grabbing surface may be hemispherical. In this embodiment, the cap remover may be grabbed without any specific orientation;
the grabbing portion may include two opposite flanges extending outwardly from the outer grabbing surface. In this embodiment, the grabbing of the outer body is more efficient.

Another aspect of the invention concerns a medical injector including:
an injector including a barrel;
a needle in communication with the barrel;
a protective cap covering the needle;
a cap remover according to the first aspect of the disclosure, the protective cap being inserting in the central opening of the cap remover.

The laminas may present a hardness at least equal to 1 time the hardness of the protective cap.

The laminas may present a Young's modulus at least equal to 60 time the Young's modulus of the protective cap.

BRIEF DESCRIPTION OF THE DRAWINGS

The above-mentioned and other features and advantages of this disclosure, and the manner of attaining them, will become more apparent, and the disclosure itself will be better understood by reference to the following descriptions of embodiments of the disclosure taken in conjunction with the accompanying drawings, wherein:

FIG. 4 is a cross section of a medical injector whose cap is inserted in a cap remover in accordance with an embodiment of the disclosure.

FIG. 5 and FIG. 6 are respectively a cross section view and a perspective view of a medical injector pulled away from a cap remover in accordance with an embodiment of the disclosure.

DESCRIPTION OF THE INVENTION

Figure 1:
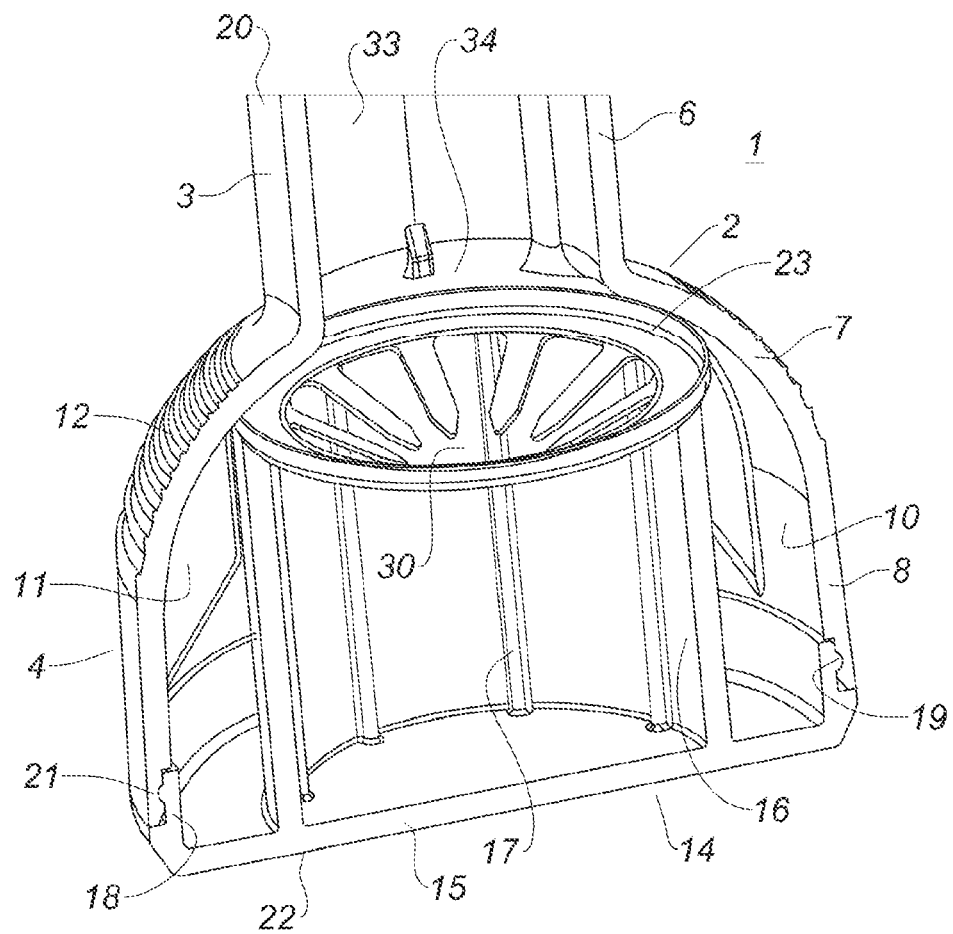
FIG. 1 is a cross section view of a cap remover in accordance with an embodiment of the present disclosure.
Figure 2:
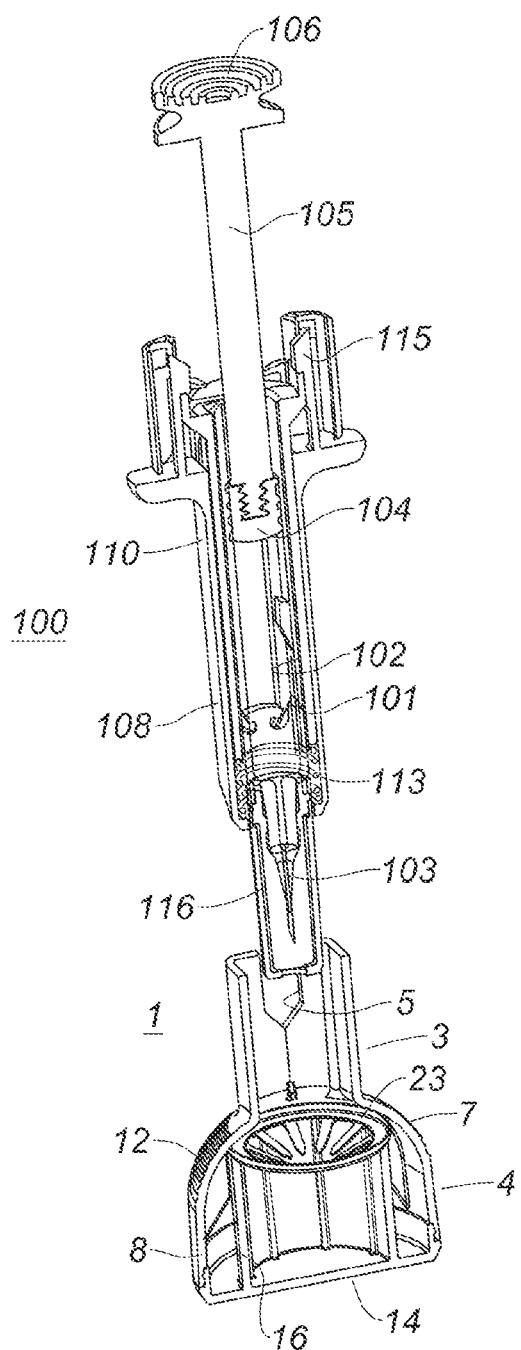
FIG. 2 and FIG. 3 are respectively a cross section view and a perspective view of a cap remover in accordance with an embodiment of the disclosure approaching a medical injector fitted with a cap.
Figure 3:
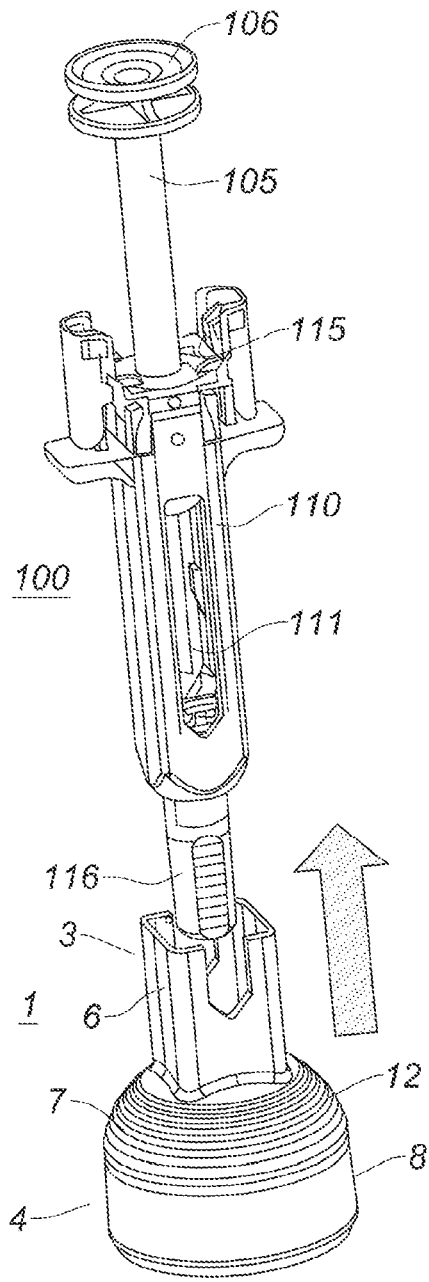

The following description is provided to enable those skilled in the art to make and use the described embodiments contemplated for carrying out the disclosure. Various modifications, equivalents, variations, and alternatives, however, will remain readily apparent to those skilled in the art. Any and all such modifications, variations, equivalents, and alternatives are intended to fall within the scope of the present disclosure.

In the following description, "distal" refers to a direction generally toward an end of a medical injector adapted for contact with a patient and/or engagement with a separate device, and "proximal" refers to the opposite direction of distal, i.e., away from the end of a medical injector adapted for engagement with the separate device. For purposes of this disclosure, the above-mentioned references are used in the description of the components of a medical injector in accordance with the present disclosure.

Referring to FIGS. 1 to 10, a cap remover 1 of the present disclosure is illustrated. The cap remover 1 is configured for removing a protective cap 116 covering a needle 103 of a medical injector. The medical injector may be a syringe, a syringe provided with a safety device, a syringe provided with a safety device and a holder device, an auto-injector or a pen injector.

In one illustrated embodiment, the cap remover 1 includes an outer body 2 including a proximal end 20 and a distal end 22. The outer body 2 is preferably made of plastic. The outer body 2 includes an insertion portion 3 at its proximal end and a grabbing portion 4 at its distal end. The insertion portion 3 defines a cavity 33 configured to guide the protective cap 116 from the proximal end 20 of the outer body 2 toward a central opening 30 sized and shaped to receive the protective cap 116.

The insertion portion 3 can include a wall 6 having a square cross section. Two opposed portions of the walls can each be provided with a longitudinal cut-out 5.

According to a first embodiment represented on FIGS. 1 to 6, the grabbing portion 4 may include a hemispherical portion 7 and an adjacent cylindrical skirt 8 defining an internal cavity 10. At its apex, the hemispherical portion 7 is provided with an opening. In the illustrated embodiment, the opening is defined by the intersection of the insertion portion 3 and the hemispherical portion 7 and is thus square shaped. In other embodiments of the disclosure (not shown), where the insertion portion 3 has a circular shape, the opening is circular. The grabbing portion 4 is provided with a series of internal ribs 11 which are radially oriented towards a central axis of the internal cavity 10.

The outer surface of the hemispherical portion 7 may include a plurality of indentations 12. In the illustrated embodiment, the indentations 12 are formed as a plurality of annular ribs and annular troughs which are integrally formed with the body 2 of the cap remover 1. The indentations 12 can also cover the cylindrical skirt 8.

Figure 11:
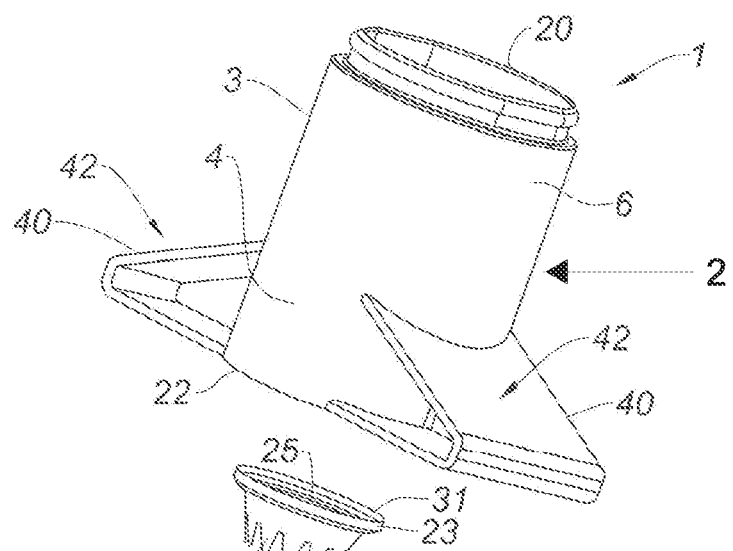
FIG. 11 is a perspective view of a cap remover in accordance with an embodiment of the present disclosure.
Figure 12:
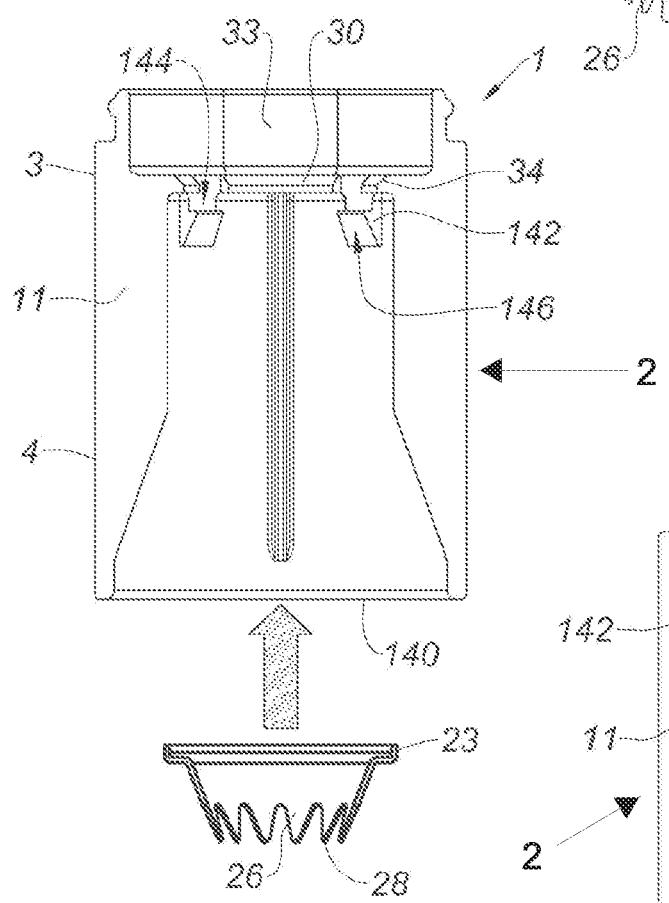
FIG. 12 and FIG. 13 are cross section views of a cap remover in accordance with an embodiment of the present disclosure.
Figure 13:
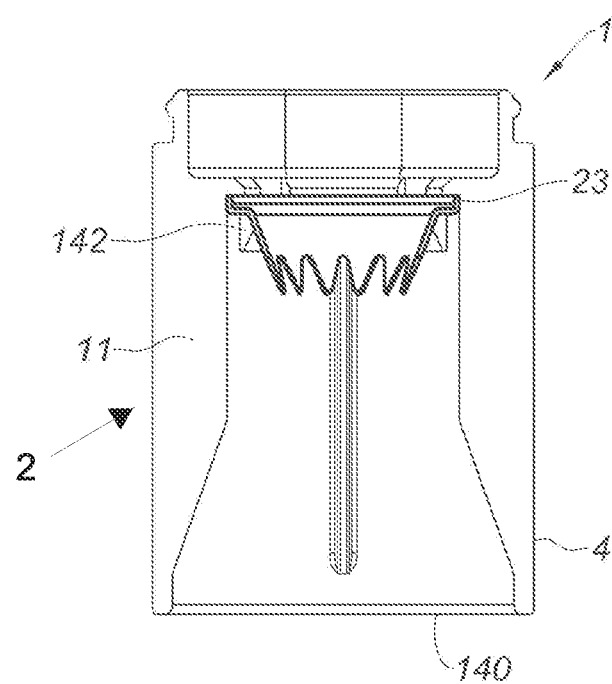

According to another embodiment shown on FIGS. 11 to 13, the grabbing portion 4 may include two radial flanges 40 extending outwardly from the outer grabbing surface. These two flanges 40 may be located at two diametrically opposite sides of the outer grabbing surface. The flanges 40 may present a proximally oriented surface 42 so as to allow placement of a user's fingers and application of a distal force, thereby facilitating removal of the cap 116.

According to the embodiment of FIGS. 11 to 13, the insertion portion 3 can include a wall 6 having a cylindrical cross section.

As visible on FIGS. 11 to 13, instead of a plug 14 which seals the distal end 22 of the body 2, said distal end 22 may delimit an access opening 140. The access opening 140 is configured to allow mounting of the extraction member 23 into the body 2. The access opening 140 is therefore dimensioned and shaped so as to allow insertion of the extraction member through said access opening 140, for example with a translational movement of the extraction member 23 along a central longitudinal axis of the cap remover 1. The body 2 may include clipping means, such as flexible hooks 142, so as to permit quick and reliable fastening of the extraction member 23 inside the body 2. The hooks 142 may include a proximally oriented axial stopping surface 144 configured to block a distal face of the annular ring 25. The hooks 142 may include a distally oriented guiding surface 146 which is inclined relative to a central longitudinal axis of the cap remover 1, so as to facilitate deformation of the hooks 142 and thus the placement of the extraction member 23.

According to both the embodiments of FIGS. 1-6 and 11-13, it should be noted that the grabbing portion 4 preferably becomes wider as one goes in the distal direction. In other words, the grabbing portion 4 at least partly flares in the distal direction, or at least partly tapers in the proximal direction.

In some embodiments, for example as represented on FIGS. 1 to 6, the distal end of the body 2 may be sealed by a distal plug 14. The distal plug 14 includes a distal circular surface 15 and circular inner wall 16. The inner wall 16 can include a series of inner ribs 17 aligned with the generatrix of the inner wall 16. The circular distal surface 15 is provided with a rim 18 wherein an annular rib 19 is formed.

The distal plug 14 is engaged and retained in the cylindrical skirt 8 of the grabbing portion 4 by engagement of the annular rib 19 into an annular groove 21 formed in the inner surface of the cylindrical skirt 8. When engaged with the grabbing portion 4, the circular inner wall 16 of the distal plug 14 extends in a proximal direction toward the insertion portion 3.

The cap remover 1 is provided with an extraction member 23 positioned within the outer body 2 between a distal end 34 of the insertion portion 3 and a proximal end of the circular inner wall 16 of distal plug 14. The extraction member 23 is metallic, and preferably made of stainless steel, for example, of 304L grade.

Figure 7:
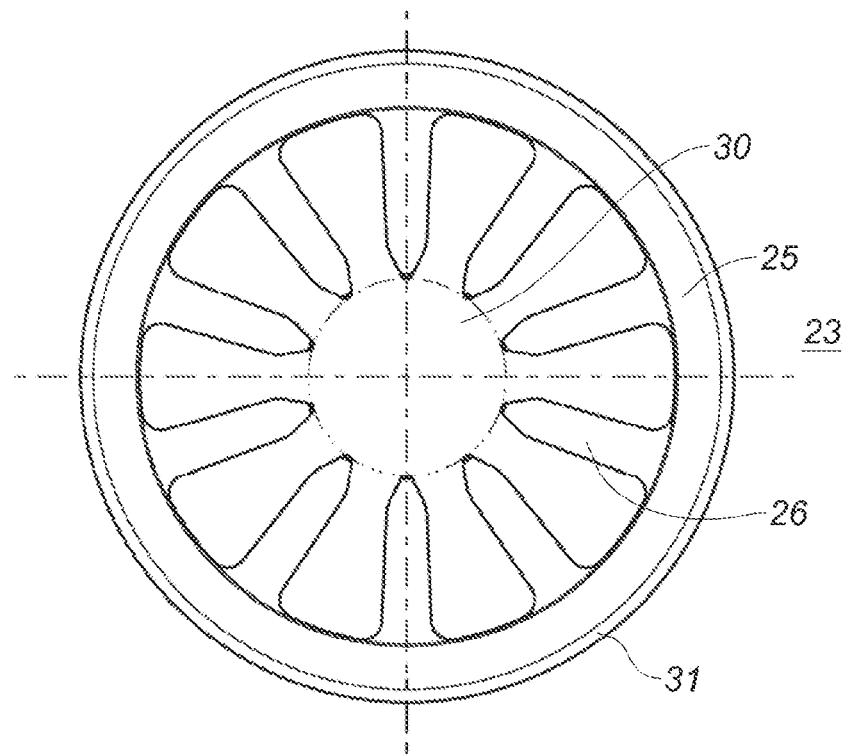
FIG. 7 is a top plan view of an extraction member in accordance with an embodiment of the disclosure.
Figure 8:
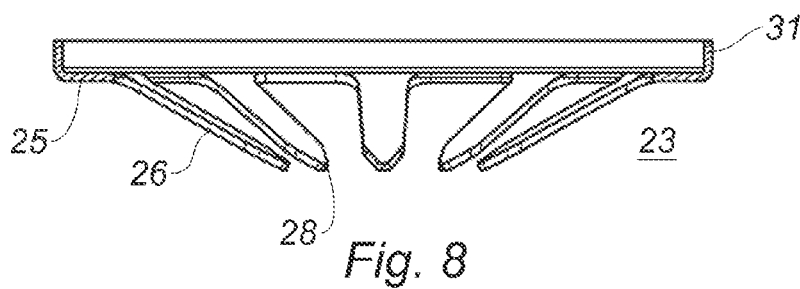
FIG. 8 is a cross section of an extraction member in accordance with an embodiment of the disclosure.

In the illustrated embodiments and as best seen on FIGS. 7 and 8, the extraction member 23 includes an annular ring 25 and a series of flexible metallic laminas 26 which protrude radially and inwardly from the annular ring 25. The laminas define a central opening 30.

The laminas 26 are configured:
to flex outwardly and slide on the protective cap 116 when the protective cap moves in the central opening 30, relatively to the outer body 2, according to a first direction. More precisely, the laminas are configured to flex outwardly and slide on the protective cap 116 when the protective cap is inserted in the central opening 30, i.e. when the protective cap moves, relatively to the outer body 2, from the proximal end of the outer body toward the distal end of the outer body; and
to stick into the protective cap 116 when the protective cap 116 moves in the central opening 30, relatively to the outer body 2, according to a second direction. More precisely, the laminas are configured to stick into the protective cap 116 when the protective cap 116 moves in the central opening 30, relatively to the outer body 2, from the distal end of the outer body toward the proximal end of the outer body.

The laminas 26 define a frustoconical envelope between the annular ring 25 and the central opening 30. The central opening 30 presents a diameter inferior to the diameter of the annular ring 23. The frustoconical envelope is oriented toward the distal end of the outer body 2. In other words, the central opening 30 is located distally from the annular ring 23.

The laminas 26 are sized so that, before insertion of the protective cap 116, the central opening 30 presents a diameter of between 78% and 95% of the diameter of the protective cap 116. This ratio between the diameter of the central opening and the diameter of the protective cap is sufficiently high so that the protective cap may slide in the central opening when it moves in the central opening 30, relatively to the outer body 2, according to the first direction. However, this ratio is sufficiently small so that the laminas may embed themselves in the protective cap when the protective cap moves in the central opening 30, relatively to the outer body 2, according to the second direction.

The extraction member 23 can include between eight and twelve laminas 26 and preferably include ten laminas 26, as disclosed on FIGS. 1 to 10, in order to center the protective cap in the central opening 30.

Each lamina is flexible. More precisely, each lamina preferably presents a stiffness of between 2 N and 30 N. To that purpose, the laminas are preferably stainless steel laminas. Each lamina preferably presents a thickness of between 0.15 mm and 0.30 mm and a length of between 4 mm and 8 mm. Alternatively, the same stiffness could be obtained with laminas in aluminium or copper.

Each lamina preferably presents a Young's modulus at least equal to 60 times the Young's modulus of the protective cap in order to be able to stick themselves into the protective cap. To that purpose, for example, when the protective cap is made of polypropylene, the laminas are preferably made of stainless steel or aluminium.

Each lamina 26 includes a sharp tip in order to stick themselves into the protective cap 116 when the protective cap moves in the second direction. The sharp tip may be formed of two converging side edges 27 connected by a distal edge 28. It can also be noted that the tip of each lamina 26 can be thinned to form a more sharpened distal edge 28.

The extraction member 23 may further include a peripheral rim 31 which is provided on the annular ring 25. The peripheral rim is positioned on the external diameter of the annular ring 25.

Figure 9:
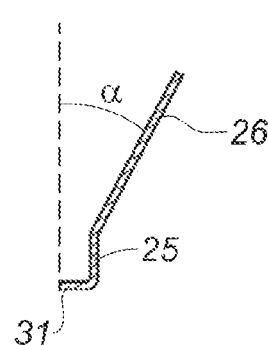
FIG. 9 is a cross section of an extraction member in accordance with an embodiment of the disclosure taken along a lamina of the extraction member.
Figure 10:
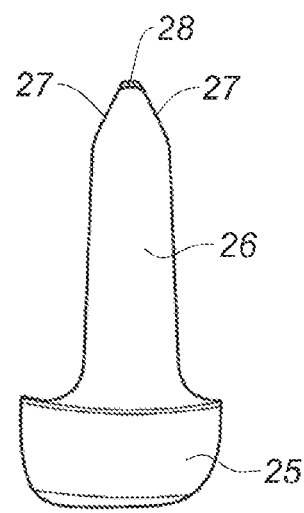
FIG. 10 is a top plan view of laminas of an extraction member in accordance with an embodiment of the disclosure.

Referring for example to FIGS. 8 and 9, the laminas 26 are positioned at an angle $\alpha$ with the annular ring 25. The angle $\alpha$ that connects the laminas 26 to the annular ring can vary between 15° and 60° and preferably is equal to 28°. This angle is chosen so that, when the protective cap moves in the central opening in the first direction with respect to the outer body, the laminas may slide on the protective cap 116, while the protective cap moves in the central opening in the second direction with respect to the outer body, the laminas embed themselves into the protective cap 116.

The laminas 26 are preferably flexibly connected to the annular ring 25. The extraction member 23 can be formed, for example, by stamping or punching a flat sheet of metal whereby the peripheral rim 31 (which can be stamped on the other side), the annular ring 25 and laminas 26 are cut, and the laminas 26 are deformed and bent to acquire their required angle with respect to the annular ring 25. The thickness of the metal sheet can be, for example, 0.25 mm so as to produce an extraction member 23 wherein the annular ring 25, the laminas 26 and the peripheral rim have a thickness of 0.25 mm. Other manufacturing techniques such as laser cutting can also be considered.

The cap remover 1 is configured to cooperate with a medical injector 100. The medical injector 100 may be of various forms, such as a syringe, self-injector, auto-injector, or pen injector, and may be configured in any known device to deliver a medicament.

A medical injector 100 can be as described as in FIGS. 2 to 6 and is represented for illustrative purpose only.

The cap remover 1 of the disclosure is configured to operate with any kind of medical injector 100 equipped with a protective cap.

As illustrated in FIGS. 2 to 6, the illustrative medical injector 100 may typically include a syringe 101 having a standard plastic or glass prefilled barrel 102 tipped with an injection needle 103, a stopper 104, and a plunger rod 105 having a flange 106.

The medical injector 100 can further include, as illustrated, an anti-needle stick safety device 108. The anti-needle stick safety device 108 can encapsulate the syringe 101 and can have a retracted position as shown in FIGS. 2 to 6 or an extended position (not shown) where the anti-needle safety device covers and shields the needle 103.

In the illustrated embodiment, the anti-needle stick safety device 108 includes an external body 110. The external body 110 can include a transparent window 111 so that the medicament contained in the syringe 101 is visible to the user.

A spring 113 is located at the distal end of the syringe 101 and is interposed between the syringe 101 and the external body 110, urging the body 110 into its extended position.

The external body 110 can include two flexible tabs 115 which engage into the barrel 102 and maintain the anti-needle stick safety device 108 in its retracted position.

The medical injector 100 can also be provided with a cap 116 which protects the needle 103 and maintains sterility when the medical injector 100 is not in use. The cap 116 can be made of a suitable plastic material such as polypropylene.

Prior to use, the cap remover 1 is engaged onto the medical injector cap 106. The grabbing portion 4 provides ergonomic surfaces that make it easy for a user to grip the cap remover 1. The grabbing portion 4, which may include a hemispherical portion 7 or two opposite flanges 40, provides an easy to grip surface even to a user who may lack finger agility, dexterity, coordination or strength.

The grabbing portion 4 allows a user to grasp the cap remover 1 and thus provides easy handling.

At first, the medical injector 100 cap is guided within the insertion portion 3. Thus, the cap 116 is centered within the insertion portion 3 during the introduction of the cap 116 in the cap remover 1. The frustoconical envelope of the laminas 26 further creates a funnel shaped surface which also contributes to an insertion of the cap remover 1 along the cap remover 1 axis. In other words, the introduction of the cap 116 into cap remover 1 is carried out in a properly aligned way. The extraction member 23 which includes between eight and twelve laminas 26 and preferably includes ten laminas 26 makes it possible to axially guide the cap into the cap remover 1.

During insertion of the protective cap into the central opening, the protective cap moves in the central opening according to the first direction, i.e. it moves from the proximal end of the end body toward the distal end of the outer body. During insertion of the protective cap into the cap remover, the protective cap 116 pushes the laminas 26 of the extraction member 23. The laminas 26 which are elastically connected to the annular ring 25 are configured to flex and thus allow the protective cap 116 to fully enter into the central opening 30.

During the insertion of the protective cap 116 in the cap remover 1, the laminas 26 slide on the surface of the protective cap.

The protective cap 116 is preferably inserted in the central opening 30 until the distal end of the protective cap 116 abuts against the distal plug 14.

Once inserted into the cap remover 1, the protective cap is preferably positioned such that the free end of the laminas are located between ¼ and ¾ of the total length of the protective cap.

When a user wants to remove the protective cap 116 to uncover the needle, he can distally pull the cap remover. The laminas 26 embed themselves in the surface of cap remover 1 and bite into the surface of the protective cap. The laminas are configured to exert a clamping force of between 20 N and 300 N.

The protective cap, which is preferably made of a plastic material such as polypropylene, provides a soft surface—when compared to the metal which the laminas 26 are made of—where the laminas 26 can at least superficially dig into.

In embodiments, the extraction member 23 made of stainless steel has a Young's modulus of 200 GPa and the cap 116 made of plastic material has a Young's modulus of 1.9 GPa.

In other words, the user can pull the cap remover 1 from the medical injector 100 as seen on FIGS. 5 and 6 and, during this operation, the cap is hooked in the within the cap remover 1 by the extraction member 23.

The medical injector 100 cap remains hooked in the cap remover 1 while a user pulls the cap remover 1 from the medical injector 100, as can be seen in FIG. 6.

The cap remover 1 provides an easy to manoeuvre device which can be operated by a wide range of users, from medical staff to untrained patients.

What is claimed is:

1. A cap remover for removing a protective cap covering a needle of a medical injector, the cap remover comprising:
   an outer body comprising:
      a proximal end and a distal end;
      an insertion portion defining a cavity configured to guide and center the protective cap from the proximal end of the outer body toward a central opening of the insertion portion sized and shaped to receive the protective cap; and
      a grabbing portion comprising two flanges extending outwardly from an outer surface of the grabbing portion; and
   an extraction member positioned within the outer body, the extraction member comprising:
      an annular ring coupled to the outer body; and
      a plurality of laminas extending radially and inwardly from the annular ring toward the central opening of the insertion portion,
      wherein the annular ring includes a peripheral rim and a distal face extending radially inward from the peripheral rim, the distal face positioned between the peripheral rim and the plurality of laminas.

2. The cap remover according to claim 1, wherein the two flanges are positioned at diametrically opposite sides of the outer surface of the grabbing portion.

3. The cap remover according to claim 1, wherein each of the two flanges comprises a proximally oriented surface so as to allow placement of a user's fingers and application of a distal force.

4. The cap remover according to claim 1, wherein the extraction member is positioned within the outer body at a distal end of the insertion portion.

5. The cap remover according to claim 4, wherein the outer body comprises a plurality of flexible hooks positioned at the distal end of the insertion portion.

6. The cap remover according to claim 5, wherein the plurality of flexible hooks is configured to couple the extraction member to the outer body.

7. The cap remover according to claim 5, wherein each of the plurality of flexible hooks comprises a proximally oriented axial stopping surface, wherein the proximally oriented axial stopping surface is configured to block a distal face of the annular ring of the extraction member.

8. The cap remover according to claim 5, wherein each of the plurality of flexible hooks comprises a distally oriented guiding surface, wherein the distally oriented guiding surface is configured to be inclined relative to a central longitudinal axis of the cap remover so as to facilitate deformation of each of the plurality of flexible hooks upon positioning of the extraction member at the distal end of the insertion portion of the outer body.

9. The cap remover according to claim 1, wherein the plurality of laminas defines a frustoconical envelope between the annular ring and the central opening of the insertion portion.

10. The cap remover according to claim 1, wherein the plurality of laminas is configured:
to flex outwardly and slide on the protective cap when the protective cap is inserted into the cap remover; and
to stick into the protective cap when the protective cap is removed from the needle.

11. The cap remover according to claim 1, wherein each lamina of the plurality of laminas includes a Young's modulus of between 190 GPa and 230 GPa.

12. The cap remover according to claim 1, wherein the annular ring defines a transversal plane, each lamina of the plurality of laminas forming an angle of between 15° and 60° with the transversal plane.

13. The cap remover according to claim 1, wherein the plurality of laminas of the extraction member comprises between eight and twelve laminas.

14. The cap remover according to claim 1, wherein each lamina of the plurality of laminas comprises a sharp tip.

15. The cap remover according to claim 1, wherein the plurality of laminas comprises a plurality of flexible metallic laminas.

16. The cap remover according to claim 1, wherein the extraction member is made of stainless steel.

17. The cap remover according to claim 1, wherein the plurality of laminas are configured to exert a clamping force of between 20 N and 300 N on the protective cap.

18. The cap remover according to claim 1, wherein the plurality of laminas are sized so that, before insertion of the protective cap, the central opening presents a diameter comprised of between 78% and 95% of a diameter of the protective cap to remove.

19. A medical injector comprising:
an injector comprising a barrel;
a needle in communication with the barrel;
a protective cap covering the needle; and
a cap remover according to claim 1, the protective cap configured to be inserted in the central opening of the insertion portion.

20. The medical injector according to claim 19, wherein each of the plurality of laminas include a Young's modulus at least equal to 60 times a Young's modulus of the protective cap.

* * * * *